United States Patent [19]

Spector

[11] Patent Number: 4,883,692
[45] Date of Patent: Nov. 28, 1989

[54] AROMATIC FOAM-PLASTIC DECORATIVE OBJECT

[76] Inventor: Donald Spector, 380 Mountain Rd., Union City, N.J. 07087

[21] Appl. No.: 296,683

[22] Filed: Jan. 13, 1989

[51] Int. Cl.$^4$ .......................... A61L 9/04; B42D 15/02
[52] U.S. Cl. ...................................... 428/16; 40/124.1; 206/457; 206/461; 229/92.8; 239/56; 239/57; 239/211; 428/17; 428/71; 428/905
[58] Field of Search ................... 428/71, 905, 15, 16, 428/17; 40/124.1; 206/457, 461; 229/92.8; 239/56, 57, 211

[56] References Cited

U.S. PATENT DOCUMENTS

| | | | |
|---|---|---|---|
| 3,991,146 | 11/1976 | Barrie | 428/71 X |
| 4,111,865 | 9/1978 | Seefried, Jr. et al. | 521/137 |
| 4,160,685 | 7/1979 | Kuroda | 428/79 X |
| 4,226,944 | 10/1980 | Stone et al. | 428/905 X |
| 4,268,557 | 5/1981 | Bracesco | 428/71 |
| 4,419,395 | 12/1983 | Sugimoto | 428/28 |
| 4,439,548 | 3/1984 | Weisman | 428/43 X |

Primary Examiner—Henry F. Epstein
Attorney, Agent, or Firm—Michael Ebert

[57] ABSTRACT

An aromatic decorative figure or other object formed of foam plastic material having dispersed throughout its cellular structure a relatively large amount of a volatile liquid fragrance. When the figure is exposed to the atmosphere, it continuously exudes the fragrance for a prolonged period, in the course of which the figure proceeds to shrink as a result of liquid loss, thereby indicating the approaching exhaustion of the fragrance. In one embodiment, the figure is created in situ by injecting a charge of a foam-forming mixture having the liquid fragrance dispersed therein into the cavity of a blister pack whose transparent blister is configured to assume the contours of the desired figure. The injected mixture expands within the cavity to form a figure which conforms to the contours of the blister and is cured therein. The resultant foam-plastic figure is effectively sealed within the pack to prevent the escape of fragrance, the pack also serving to display and protect the figure.

10 Claims, 1 Drawing Sheet

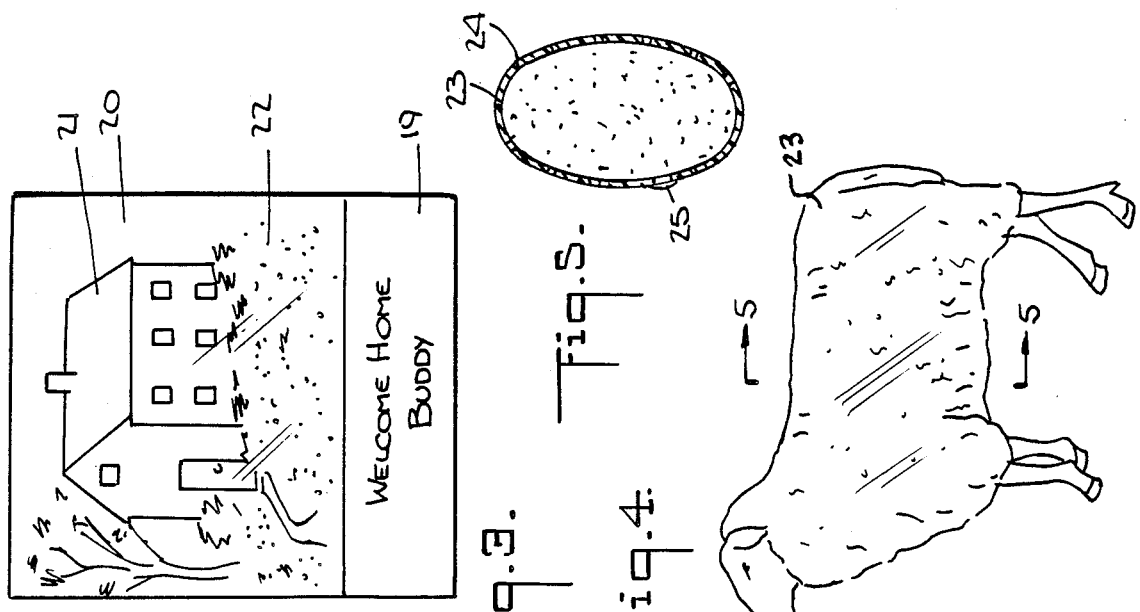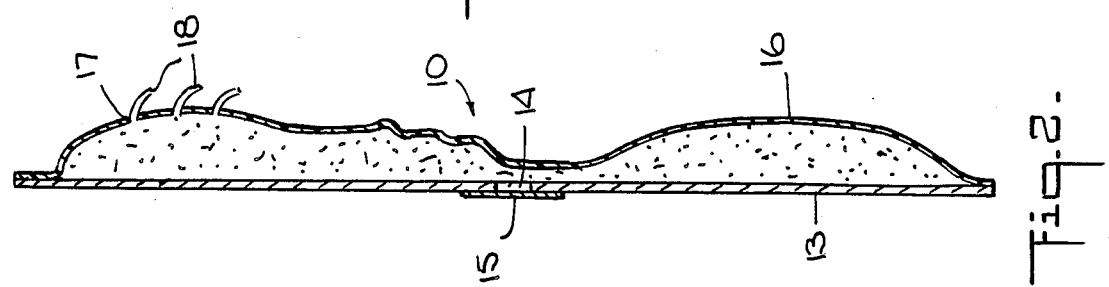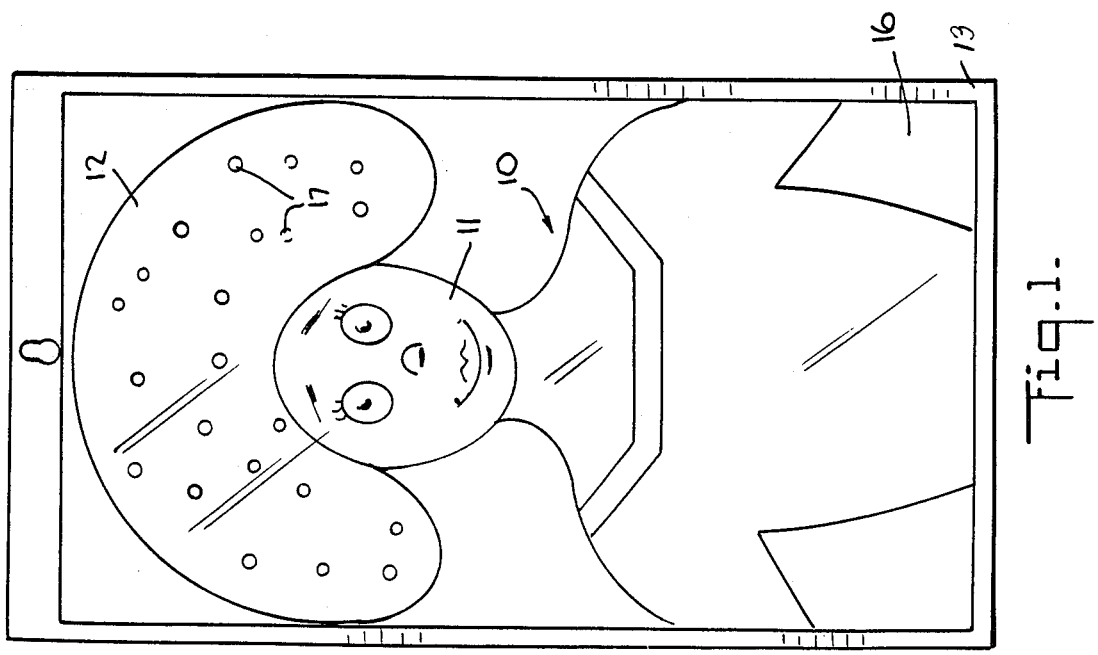

AROMATIC FOAM-PLASTIC DECORATIVE OBJECT

BACKGROUND OF INVENTION

1. Field of Invention

This invention relates generally to foam-plastic aromatic figures and other decorative objects, and more particularly to a technique for forming an in situ figure of this type within the cavity of a blister pack which initially functions as a mold therefor and then as a protective display package.

2. Status of Prior Art

Foam plastic material can be made in various densities and in varying degrees of resilience and hardness, so that the material can be soft and spongy, semi-flexible or hard and rigid. To produce a plastic foam material having a myriad of open cells, use may be made for this purpose of a blowing agent that generates gas through thermal decomposition in the polymer liquid or melt, or gas may be injected into the melt which expands during pressure relief. Gas may also be generated as a by-product of a chemical condensation reaction during cross-linking.

Various types of foam-forming polymer mixtures are disclosed in the Seefried U.S. Pat. No. 4,111,865, and in the Weisman U.S. Pat. No. 4,439,548. The invention is not limited to any one form of foam plastic material, for to create a foam plastic figure, use may be made of polyurethane, polyvinyl or any other known form of foam material which has dispersed therein a volatile liquid fragrance that is exuded when the figure is exposed to the atmosphere.

The concern of the present invention is with an article in the form of a decorative figure or other attractive object made of foam plastic material that has dispersed therein a volatile liquid fragrance, whereby the article is capable of exuding the fragrance continuously for a prolonged period.

A decorative sponge-like object of this type can be created with existing techniques by injecting the foam-forming mixture that incorporates the liquid fragrance into a shaped mold having the appropriate configuration. Because of the gas generated, the mixture expands in the mold to conform to the contours thereof, and it then cures in the mold to form the desired object. Finally, the object is removed from the mold and suitably packaged.

The problem encountered when seeking to produce shaped sponge-like objects of foam plastic material is that the cycle time for forming the sponge is considerably longer than with ordinary plastics which do not expand within the mold. Hence the cost per shot is substantially greater than it would be for a regular injection molding operation. Moreover, foam-forming materials used in the molding process are somewhat toxic prior to the sponge reaction and therefore have to be handled in a special environment. To further complicate matters, setting up machines to operate on foam requires many hours of transition time from the normal everyday injection molding process.

It is known to package toy figures and other articles of merchandise in a so-called blister pack. This pack is formed by a film or blister of clear plastic that is vacuum molded to conform generally to the configuration of the shaped article to be packaged. The margin of this blister is bonded to a backing sheet, thereby sealing the article within the blister.

The advantage of a blister pack over a conventional package is that it not only protects the article contained therein against contamination, but it also serves to display the article, so that potential purchasers are able to see the article being offered for sale. After purchase, the blister is detached from its backing sheet to release the article from the pack.

SUMMARY OF INVENTION

In view of the foregoing, the main object of this invention is to provide a decorative figure or object formed of foam plastic material which has dispersed throughout its cellular structure a substantial supply of a volatile liquid fragrance, whereby the figure when exposed to the atmosphere continuously exudes fragrance for a prolonged period.

A significant feature of the invention is that as the fragrance is exuded from the figure, the resultant loss of liquid causes the figure to shrink, thereby indicating the approaching exhaustion of the fragrance.

More particularly, an object of this invention is to provide a technique for producing an in situ figure of the above type within a mold formed by the cavity of a blister pack whose blister is configured to assume the contours of the desired figure whereby the pack serves initially as a mold to create the figure and then as a protective display package therefor.

Also an object of the invention is to provide a blister pack functioning as a mold for the aromatic foam plastic figure, the blister having apertures therein through which are extruded filaments of the expanding foam-forming mixture injected into the mold, whereby in the resultant figure these filaments simulate hair, grass, or other strands which exude fragrance.

Still another object of the invention is to provide a transparent casing contoured to provide a three-dimensional mold having the shape of a desired aromatic article, a charge of a foam-forming aromatic mixture being injected into the casing which is provided with apertures whereby when the mixture expands to fill the mold to form the object mass, strands are extruded through the apertures which exude the fragrance of the liquid dispersed in the object, the mass of the article serving as a reservoir for the liquid fragrance.

Briefly stated, these objects are attained in an aromatic decorative figure or other object formed of foam plastic material having dispersed throughout its cellular structure a relatively large amount of a volatile liquid fragrance. When the figure is exposed to the atmosphere, it continuously exudes the fragrance for a prolonged period, in the course of which the figure proceeds to shrink as a result of liquid loss, thereby indicating the approaching exhaustion of the fragrance.

In one embodiment of the invention, the figure is created by injecting a charge of a foam-forming mixture having the liquid fragrance dispersed therein into the cavity of a blister pack whose transparent blister is configured to assume the contours of the desired figure. The injected mixture expands within the cavity to form a figure which conforms to the contours of the blister and is cured therein. The resultant form-plastic figure is effectively sealed within the pack to prevent the escape of fragrance, the pack also serving to display and protect the figure.

BRIEF DESCRIPTION OF FIGURES OF DRAWING

For a better understanding of the invention as well as other objects and further features thereof, reference is made to the following detailed description to be read in conjunction with the accompanying drawings, wherein:

FIG. 1 is a front view of a blister pack in accordance with the invention in which there is contained a three-dimensional aromatic figure;

FIG. 2 is a longitudinal section taken through the pack;

FIG. 3 is a front view of a greeting card having a blister pack containing a three-dimensional house and a grass lawn;

FIG. 4 shows an aromatic foam plastic figure in the form of a lamb disposed within a transparent casing having apertures therein from which filaments are extruded to simulate the wool of the lamb; and FIG. 5 is a transverse section taken through FIG. 5 in the plane indicated by lines 5—5 in FIG. 4.

DESCRIPTION OF INVENTION

As used herein, the term "aroma" or "fragrance" is not limited to pleasant or savory smells, but encompasses scents that function as insecticides, air fresheners, deodorants or any other odor that acts to condition, modify or otherwise charge the atmosphere.

The aroma of perfumes and perfume-based products such as colognes and toilet waters was originally derived from the essential oils of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents the ingredients are combined with alcohol.

Blister Pack

Referring now to FIGS. 1 and 2, there is shown a blister pack in accordance with the invention that serves as a mold to create an in situ foam plastic aromatic figure which in the example illustrated is a girl 10 on whose head 11 is a large mass 12 of hair. The figure is encased in the pack which functions to protect and display the figure.

The pack includes a backing card 13 having a port 14 therein which is closable by a pressure-sensitive adhesive seal 15 that normally closes the port and which can be removed temporarily to open it for the admission of a foam-forming mixture. Card 13 is preferably of cardboard having a thin layer of thermoplastic PVC material coated thereon.

Thermally or otherwise bonded at its margins to backing card 17 is a blister 16 formed of a transparent synthetic plastic film, such as polyvinyl chloride, which is thermally bondable to the backing card. Blister 16 is vacuum molded or otherwise configured to assume the three-dimensional contours of FIG. 10. The blister is provided in the region of the hair mass 12 with a multitude of minute apertures 17 which are dispersed throughout the region.

The cavity defined between the contoured blister 16 and the backing card 13 is used as a mold to form figure 10 in situ. Injected into this mold through rear port 14 is a charge of a foam-forming mixture having dispersed therein a volatile liquid fragrance, which in practice, may represent as much as 30% by volume of the mixture. The amount of charge is appropriate to the final dimensions of the figure. When injected into the cavity, because of the gas which is then generated, the mixture expands to fill the cavity, and then proceeds to cure.

Apertures 17 initially function to relieve the pressure of the gas, the expanding foam plastic material after filling the cavity being extruded through these apertures to create small hair-like tentacles 18. Blister 16 is printed and colored to define the outline of the figure and to impart appropriate colors thereto.

The aromatic liquid dispersed in the cellular structure of the foam plastic figure is not permitted to escape from the sealed blister pack except through the exposed tentacles 18. Hence while the foam-plastic figure, when encased in the blister pack, is effectively sealed thereby, its aroma can be sensed by the fragrance exuded from the tentacles. In the example shown, this aroma is preferably related to the nature of the hair, so that if the hair has the color of strawberries, the aroma may be that of strawberries.

The blister pack functions as a protective package for the foam-plastic figure which displays the figure. But when the figure is removed from the pack to function as a decorative air freshener in a room or other environment, it then gives off a much greater amount of aromatic vapor which is exuded from the entire surface of the figure. Because of the large volume of aromatic liquid entrapped in the figure, as the fragrance is exuded therefrom, the figure proceeds to shrink, and in doing so indicates the degree to which the supply of aroma approaches the point of exhaustion. Thus the user is made aware of the extent to which the figure remains effective as an air freshener.

Greeting Card

The blister pack concept for molding a synthetic plastic aromatic foam article or figure may be realized in an aromatic greeting card format, as shown in FIG. 3. In this embodiment, the backing card 19 has printed thereon "Welcome Home, Buddy" or whatever text is appropriate to the greeting card.

Marginally secured to the upper section of backing card 19 is a shaped, transparent blister 20 which in the example shown defines a house 21 and a grass lawn 22 in front of the house. The card is provided with a sealable port (not shown) to admit a charge of a foam-forming mixture, and the blister is provided in the region of the grass lawn with a multitude of minute apertures from which grass-like tentacles are extruded.

The aromatic content of the foam-forming mixture injected into the cavity defined by the blister has the fragrance of grass so that the greeting card exudes this characteristic aroma.

In this embodiment, the foam plastic body molded and cured within the cavity in the greeting card is not removed therefrom, but the body serves as a reservoir for the liquid fragrance which is exuded only from the exposed grass-like tentacles. Thus unlike conventional greeting cards which are usually disposed of not long after they are received, a greeting card in accordance with the invention will usually be retained by the recipient as long as it continues to give off an aroma. This period will be relatively prolonged because of the aroma reservoir.

In practice, the aromatic foam-plastic decorative object encased in the greeting card blister may be in any decorative form, such as a cluster of flowers which exude a flower-like aroma through minute apertures or die cuts in the blister.

Encased Figure

As shown in FIGS. 4 and 5, one may create a transparent mold cavity for a figure which in the example shown is a baby lamb by means of a casing 23 of transparent, synthetic plastic film material molded to assume the three-dimensional form of the lamb.

In this instance, the foam plastic used has the hue of white lamb's wool. Distributed throughout the entire surface of casing 23 are minute apertures 24 so that the foam plastic extruded through these apertures when the foam expands in the molded cavity formed by the casing then simulates wool covering the entire body of the lamb figure.

Casing 23 is provided with a port 25 (and a removable seal therefor) into which a charge of the aromatic foam-forming mixture is injected as in the previous embodiments.

In this instance, the encased foam-plastic body of the lamb serves as a reservoir for the liquid fragrance which is exuded only from the wool-like tentacles on the exterior of the casing.

Thus in all embodiments of the invention, the foam-plastic aromatic figure or object is formed in situ within a shaped envelope in a blister, a casing or any other format, at least the front portion of the envelope being transparent to expose the object to view. Because of the high liquid fragrance content of the article, as the fragrance approaches exhaustion, it proceeds to shrink to indicate the loss of fragrance.

An example of a suitable foam-forming mixture for use in creating in situ foam plastic figures in the manner disclosed herein is HYPOL. This is a foamable hydrophilic prepolymer which is described by its manufacturer, the Organic Chemical Division of W.R. Grace & Company of Lexington, Mass., in its "Technical Bulletin C-7."

As pointed out in this bulletin, mold release agents are generally required, these being sprayed or soaked into the mold prior to use. But instead, a mold release agent, such as an oil, may be incorporated as an additive in the foam-forming formulation.

In the present invention, the oil in the fragrance added to the mixture also serves as a mold release agent. Hence when the foam plastic figure is created in situ in the cavity of the blister pack, the oil serves as a release agent; and when the figure is completed, it may be removed by rupturing the blister pack.

While there have been shown and described preferred embodiments of aromatic foam-plastic decorative objects in accordance with the invention, it will be appreciated that many changes and modifications may be made therein without, however, departing from the essential spirit thereof.

I claim:

1. An aromatic, foam-plastic, decorative, three-dimensional article comprising:
    (a) an envelope configured to assume the contoured three-dimensional form of a decorative object, said envelope forming a mold cavity and having a port therein to admit a charge of foam-forming mixture having a liquid fragrance dispersed therein which expands under gas pressure to ill said cavity and conform to the contours of the envelope, aid envelope having minute apertures therein to relieve aid gas; and
    (b) a foam-plastic object formed in situ in the cavity from said mixture admitted through said port and conforming to the contours of the envelope, aid object exuding said fragrance and said envelope being at least partially transparent to expose the object.

2. An article as set forth in claim 1, wherein said mixture as it expands is extruded through said apertures to form tentacles which project outside of the envelope and exude said fragrance.

3. An article as set forth in claim 1, further including a pressure-sensitive adhesive seal covering said port.

4. An article as set forth in claim 1, wherein said envelope is constituted by a blister pack formed by a backing card having said port therein, and a transparent blister configured to assume the form of said object and having said apertures therein, said blister being marginally bonded to said card.

5. An article as set forth in claim 4, wherein said card is coated with a film of polyvinyl chloride and said blister is formed of polyvinyl chloride whose margin is thermally bonded to the card.

6. An article as set forth in claim 4, wherein said object is a human figure.

7. An article as set forth in claim 4, wherein said figure is a human figure with hair, and said expanding mixture is extruded through said apertures to form hair-like tentacles.

8. An article as set forth in claim 4, wherein said backing card is a greeting card and said blister is marginally bonded to one section of the card, the remaining section being reserved for greeting card text and graphics.

9. An article as set forth in claim 8, wherein said object includes a grass lawn and said expanding mixture is extruded through said apertures to form grass-like tentacles.

10. An article as set forth in claim 1, wherein said envelope is a transparent casing of synthetic plastic material configured to assume the form of said object.

* * * * *

UNITED STATES PATENT OFFICE
CERTIFICATE OF CORRECTION

Patent No. 4,883,692　　　　　　　　Dated Nov. 28, 1989

Inventor(s) Donald Spector

It is certified that error appears in the above-identified patent and that said Letters Patent is hereby corrected as shown below:

Column 6, line 11, "ill" should read -fill--.

Column 6, line 13, "aid" should read --said--.

Column 6, line 17, "aid" should read --said--.

Signed and Sealed this

Thirtieth Day of October, 1990

Attest:

HARRY F. MANBECK, JR.

Attesting Officer　　　Commissioner of Patents and Trademarks